(12) United States Patent
Cole et al.

(10) Patent No.: US 6,521,237 B2
(45) Date of Patent: *Feb. 18, 2003

(54) SKIN CARE COMPOSITION

(75) Inventors: Curtis A. Cole, Langhorne, PA (US); Laura E. Flack, Overland Park, KS (US); Claudia Kaminski, Milford, NJ (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/325,452

(22) Filed: Jun. 3, 1999

(65) Prior Publication Data

US 2002/0048591 A1 Apr. 25, 2002

Related U.S. Application Data

(60) Provisional application No. 60/107,956, filed on Nov. 12, 1998.

(51) Int. Cl.[7] .............................. A61K 6/00; A61K 7/00
(52) U.S. Cl. ..................... 424/401; 424/400; 424/59; 424/60; 424/450; 424/489; 424/47
(58) Field of Search ................................ 424/400, 401, 424/59, 47, 60, 450, 489

(56) References Cited

U.S. PATENT DOCUMENTS

| 5,554,647 | A | 9/1996 | Perricone |
| 5,643,586 | A | 7/1997 | Perricone |
| 5,646,186 | A | 7/1997 | Wang et al. ................ 514/557 |
| 5,665,776 | A | 9/1997 | Yu et al. ..................... 514/557 |
| 5,679,374 | A | 10/1997 | Fanchon et al. |
| 5,744,148 | A | 4/1998 | Habif et al. |
| 5,879,690 | A | 3/1999 | Perricone |
| 5,889,054 | A | 3/1999 | Yu et al. ..................... 514/557 |
| 5,942,250 | A | 8/1999 | Yu et al. ..................... 424/481 |

OTHER PUBLICATIONS

U.S. patent application Ser. No. 09/565,716, pending.
U.S. patent application Ser. No. 09/436,867, pending.
Neutrogena Pore Refining Cream, 1 oz. size product packaging, launched May 11, 1999.

*Primary Examiner*—Dameron L. Jones
(74) *Attorney, Agent, or Firm*—William E. McGowan

(57) ABSTRACT

There are provided compositions which include a retinoid and preferably retinol; an acid; and an acid neutralizing effective amount of ammonium hydroxide. There are also provided compositions which include a retinoid and a neutralized ammonium salt of an acid. Further provided are methods for reducing fine lines and wrinkles and for increasing the clarity of a skin surface, cellular turnover, skin radiance, skin smoothness, skin permeation or collagen synthesis in a mammal in need thereof. Compositions as described above are administered topically to the skin of the animal.

38 Claims, 3 Drawing Sheets

SKIN CARE COMPOSITION

This patent application claims the priority of U.S. provisional patent application No. 60/107,956 filed Nov. 12, 1998 which is incorporated herein by reference.

FIELD OF THE INVENTION

This invention relates to skin care compositions which include, in a single formulation, the beneficial ingredients for aging or photodamaged skin, retinol and an acid.

BACKGROUND OF THE INVENTION

Retinol or vitamin A alcohol is useful in the reduction of fine lines, wrinkles, and mottled hyperpigmentation in skin. Hydroxy acids, and particularly alpha-hydroxy acids, are useful in increasing the clarity of the skin surface, increasing cellular turnover, and increasing skin radiance and smoothness. Ascorbic acid has skin permeation and collagen synthesis activity.

However, retinol is physically unstable and rapidly degrades when stored at a pH below about 5. Acids such as hydroxy acids, and particularly alpha-hydroxy acids and ascorbic acid, on the other hand, are not active in increasing skin cell turnover, exfoliation, skin permeation, and/or collagen synthesis at pHs above about 5, however.

Consequently, retinol and hydroxy acids and/or ascorbic acid have generally been packaged separately. Retinol typically is packaged in a vehicle at a pH above about 5, while alpha-hydroxy acids and ascorbic acid are packaged at a pH of about 4 or below. Therefore, one must apply two separate products in order to achieve the benefit of both of these ingredients.

The present inventors have discovered a single composition which include both of these ingredients, in which both of these ingredients are stable, and in which both of these ingredients are active upon application to the skin.

SUMMARY OF THE INVENTION

Figure 1:
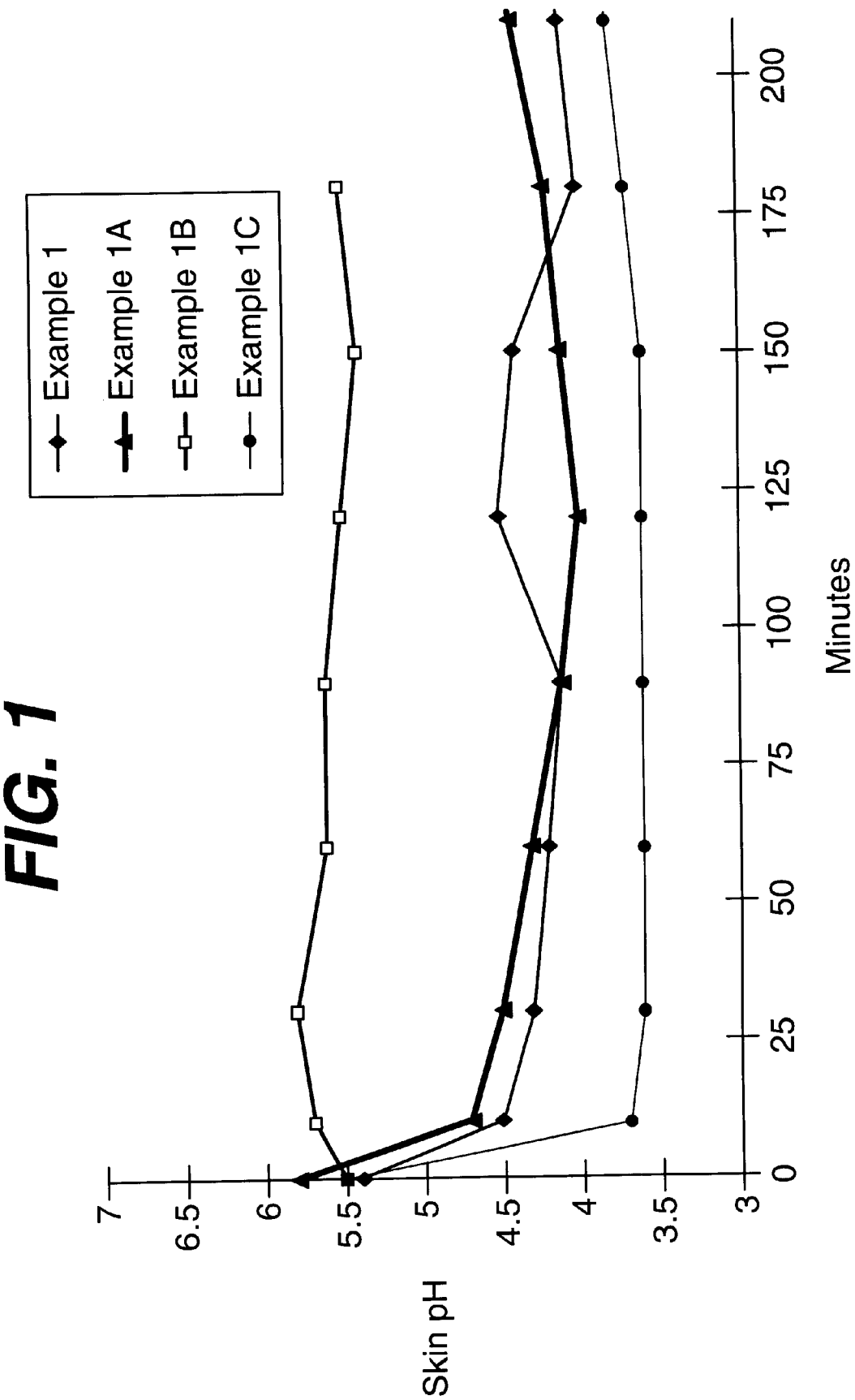
FIG. 1 is a graphic illustration of skin pH over time after treatment.

According to one embodiment of the present invention there are provided compositions which include:

(A) a retinoid and preferably retinol;

(B) an acid selected from the group consisting of a hydroxy acid, ascorbic acid, or a combination thereof; and (C) an acid neutralizing effective amount of ammonium hydroxide.

According to an alternate embodiment of the present invention, there are provided compositions which include:

(A) retinol; and (B) a neutralized ammonium salt of an acid selected from the group consisting of a hydroxy acid, ascorbic acid, or a combination thereof.

Further provided are methods for reducing fine lines and wrinkles and for increasing the clarity of a skin surface, cellular turnover, skin radiance and skin smoothness in an animal in need thereof. Compositions as described above are administered topically to the skin of the animal.

DETAILED DESCRIPTION OF THE INVENTION

The present formulations provide compositions which have a storage pH of about 5 or higher. This provides storage stability for the retinol compound. However, the pH of these compositions drops to below 5 when applied to the skin. This allows the hydroxy acid(s) therein to become active upon application of the composition to the skin.

Retinoids suitable for use in the present invention preferably are unstable or pH sensitive in that they are chemically and physically unstable at relatively low pH such as, for example a pH below about 5. Such retinoids include, but are not limited to retinol, retinoic acid, retinaldehyde, and like compounds that bind to retinoid receptors.

Retinol is also known as vitamin A alcohol. Retinol is chemically and physically unstable at a pH below about 5. It is useful in reducing fine lines at wrinkles in skin. It is also useful in reducing mottled hyperpigmentation of skin. Other retinoids having pH dependent stability may also be used in combination with or in place of retinol in the present invention.

Hydroxy acids useful in the present invention are either alpha- or beta-hydroxy acids, poly-hydroxy acids, poly alpha-hydroxy acids or any combinations of any of the foregoing. Preferably, the hydroxy acid is an alpha-hydroxy acid. Examples of alpha hydroxy acids include, but are not limited to, glycolic acid, malic acid, tartaric acid, pyuric acid, or any combination of any of the foregoing. Special mention is made of glycolic acid.

Beta-hydroxy acids include, but are not limited to, salicylic acid.

Other acids suitable for use in the present invention include, but are not limited to, ascorbic acid.

Ammonium hydroxide is typically added as a solution of a pH of about 6 and containing from about 27 to about 31 percent by weight of ammonium hydroxide based upon 100 percent by weight of total ammonium hydroxide solution.

The compositions of the present invention may also include, for example, vehicles including, but not limited to, water or alcohol; humectants, including, but not limited to, glycerin; buffering agents including, but not limited to, citric acid and sodium citrate; viscosity adjusters, including, but not limited to, carbomer gelling agents, gum derivatives, and the like; preservatives including, but not limited to, methylparaben, propylparaben, and phenoxyethanol; emulsifiers including, but not limited to, polysorbitate 80, glyceryl distearate, POE 10 stearyl ether, ceateareth 20 and stearyl alcohol, and cetaereth 20 and cetearyl alcohol; conditioning agents including, but not limited to, octyl hydroxystearate; emollients including, but not limited to, cholesterol NF, petrolatum, mineral oils and esters including, but not limited to, isopropyl myristate, isopropyl palmitate, 1-decene polymer (hydrogenated), and $C_{12}$–$C_{15}$ alcohol benzoates; thickness, including, but not limited to, polyacrylamide, $C_{13}$–$C_{14}$ isoparafin, and laureth-7; antioxidants, including, but not limited to ascorbic acid, (BHT), tocopheryl acetate, and the like; UV stabilizers; UV radiation absorbers (sunscreen filters); fragrances; colorants; or any combinations of any of the foregoing.

These compositions can be formulated as creams, gels, or liquids, and preferably are prepared as lotions. Compositions can be prepared as multi-lamellar vesicles, liposomes, nanospheres, microsponges, or any combination of any of the foregoing by methods known to those skilled in the art.

The neutralized ammonium salt of the acid is typically neutralized to a pH above about 4.5, preferably ranging from about 4.5 to about 8 and most preferably from about 5 to about 6. The amount of ammonium hydroxide useful herein in that amount sufficient to adjust the pH of the acid to the above pH ranges.

The amount of retinol in these compositions is typically a fine line-, wrinkle-, or mottled pigmentation-reducing effective amount. Preferably, the amount of retinol is at least about 0.01 percent by weight, and most preferably, is at least about 0.15 percent by weight, based upon 100 percent by weight of total composition.

The amount of acid or ammonium salt of acid is typically a skin surface clarity, cellular turnover-, skin radiance-, skin smoothness-, skin permeation-, or collagen synthesis-increasing effective amount. Preferably, this amount ranges from about 0.1 to about 12 percent by weight based, upon 100 percent by weight of total composition. Most preferably, this amount is about 4 percent by weight, based upon 100 percent by weight of total composition.

Without being bound by any theory, applicants believe that by using the ammonium salt of the acid, the storage pH of the present composition can remain above 5, thereby providing a stable atmosphere for the retinol or any other pH sensitive ingredient. However, when applied to the skin, the pH of the ammonium salt of the acid changes by volatilization of the ammonium. The pH drops to a range in which the acid can cause beneficial changes.

The compositions can be applied topically to a mammal, and preferably a human, in need of a retinoid, acids, or a combination thereof. Typically, the amount applied will be that amount effective to accomplish the purpose of application.

DESCRIPTION OF THE PREFERRED EMBODIMENT

The following examples illustrate the invention without limitation. All amounts are given as weight percentages based upon 100 percent by weight of total composition unless noted otherwise.

EXAMPLE 1

A retinol/alpha-hydroxy acid containing composition having the formulation of Table 1 and a pH of about 6 was prepared in the form of multi-lamellar vesicles.

TABLE 1

Retinol/Alpha-Hydroxy Acid Liposome Formulation-pH6

| TRADE NAME | CHEMICAL NAME (qs with DI water) | FUNCTION | % WT/WT |
|---|---|---|---|
| AQUEOUS PHASE | | | |
| Deionized Water | D.I. Water | Vehicle | 60.93 |
| Glycerin 916 | Glycerin | Humectant | 4 |
| Citric Acid | Citric Acid | Buffering Agent | 0.13 |
| Sodium Citrate | Sodium Citrate | Buffering Agent | 0.5 |
| Sodium Chloride | Sodium Chloride | Viscosity Adjuster | 0.1 |
| Methyl Parasept | Methylparaben | Preservative | 0.25 |
| Propyl Parasept | Propylparaben | Preservative | 0.15 |
| Tween 80 | Polysorbate 80 | Emulsifier | 0.7 |
| Glypure (70%) | Glycolic Acid | Skin Conditioner | 5.71 |
| NH4OH | Ammonium Hydroxide (27 to 31% Solution) | pH Adjuster (pH = 6) | 3.2 |
| LIPID PHASE | | | |
| Wickenol 171 | Octyl Hydroxystearate | Conditioning Agent | 5.8 |
| Kessco GDS* | Glyceryl Distearate | Emulsifier | 2.8 |
| Cholesterol, NH* | Cholesterol NF | Emulsifer | 1 |
| BRIJ 76* | POE 10 Stearyl Ether | Emulsifier | 1.4 |
| Protocol ST 20G | Ceteareth 20 and Stearyl Alcohol | Emulsifier | 3 |
| Protocol CS 20D | Ceteareth 20 and Stearyl Alcohol | Emulsifier | 3 |
| Stearyl Alcohol | Stearyl Alcohol | Skin Conditioner | 0.5 |
| Vitamin A Alcohol Blend** | Retinol in Polysorbate | Skin Conditioner | 0.4 |
| BHT | BHT | Antioxidant | 0.1 |
| Vitamin E Acetate | Tocopheryl Acetate | Antioxidant | 0.1 |
| SINGLE ADDITIONS | | | |
| Emeressence 1160 | Phenoxyethanol | Preservative | 0.73 |
| Dimethicone 47V | 100 Centistoke Dimethicone | Skin Conditioner | 2.5 |
| Sepigel 305 | Polyacrylamide, C13–24 Isoparrifin and Laureth-7 | Thickener | 3 |

*Ingredients responsible for the formation of multi-lamellar vesicles
**This formula contains a 15% overage of retinol. Retinol assay value = 43.28%
Amount of NH₄OH required to reach pH of 6 is estimated; each batch will be titrated to pH = 6.

The formulation was applied to the skin, and the pH of the skin was measured over time. Results are illustrated in FIG. 1. The pH of the preparation dropped to about 4.1 within 15 minutes of the application. This reduced the skin pH to about 4.

COMPARATIVE EXAMPLE 1A

A retinol/alpha-hydroxy acid containing composition having the formulation of Table 2 and a pH of about 4 was prepared in the form of multi-lamellar vesicles.

TABLE 2

Retinol/Alpha-Hydroxy Acid Liposome Formulation - pH4

| TRADE NAME | CHEMICAL NAME (qs with DI water) | FUNCTION | % WT/WT |
|---|---|---|---|
| AQUEOUS PHASE | | | |
| Deionized Water | D.I. Water | Vehicle | 62.43 |
| Glycerin 916 | Glycerin | Humectant | 4 |
| Citric Acid | Citric Acid | Buffering Agent | 0.13 |
| Sodium Citrate | Sodium Citrate | Buffering Agent | 0.5 |
| Sodium Chloride | Sodium Chloride | Viscosity Adjuster | 0.1 |
| Methyl Parasept | Methylparaben | Preservative | 0.25 |
| Propyl Parasept | Propylparaben | Preservative | 0.15 |
| Tween 80 | Polysorbate 80 | Emulsifier | 0.7 |
| Glypure (70%) | Glycolic Acid | Skin Conditioner | 5.71 |
| NH₄OH | Ammonium Hydroxide 27 to 31% Solution | pH Adjuster (ph = 4) | 1.7 |

TABLE 2-continued

Retinol/Alpha-Hydroxy Acid Liposome Formulation - pH4

| TRADE NAME | CHEMICAL NAME (qs with DI water) | FUNCTION | % WT/WT |
|---|---|---|---|
| LIPID PHASE | | | |
| Wickenol 171 | Octyl Hydroxystearate | Conditioning Agent | 5.8 |
| Kessco GDS* | Glyceryl Distearate | Emulsifier | 2.8 |
| Cholesterol, NH* | Cholesterol NF | Emollient | 1 |
| BRIJ 76* | POE 10 Stearyl Ether | Emulsifer | 1.4 |
| Protocol ST 20G | Ceteareth 20 and Stearyl Alcohol | Emulsifier | 3 |
| Protocol CS 20D | Ceteareth 20 and Stearyl Alcohol | Emulsifier | 3 |
| Stearyl Alcohol | Stearyl Alcohol | Skin Conditioner | 0.5 |
| Vitamin A Alcohol Blend** | Retinol in Polysorbate | Skin Conditioner | 0.4 |
| BHT | BHT | Antioxidant | 0.1 |
| Vitamin E Acetate | Tocopheryl Acetate | Antioxidant | 0.1 |
| SINGLE ADDITIONS | | | |
| Emeressence 1160 | Phenoxyethanol | Preservative | 0.73 |
| Dimethicone 47V | 100 Centistoke Dimethicone | Skin Conditioner | 2.5 |
| Sepigel 305 | Polyacrylamide, $C_{13-24}$ Isoparrifin and Laureth-7 | Thickener | 3 |

*Ingredient Responsible for the formation of multi-lamellar vesicles
**This formula contains a 15% overage of retinol. Retinol assay value = 43.28%
  Amount of NH$_4$OH required to reach pH of 4 is estimated.

The formulation was applied to skin, and the pH of the skin was measured over time. Results are illustrated in FIG. 1.

COMPARATIVE EXAMPLE 1B

A retinol/alpha-hydroxy acid containing composition is prepared as in Example 1, substituting sodium hydroxide for the ammonium hydroxide.

The formulation was applied to skin, and the pH of the skin was measured over time. Results are illustrated in FIG. 1.

COMPARATIVE EXAMPLE 1C

An alpha-hydroxy acid containing composition having 8 percent by weight sodium glycolate at a pH of 3.5 and no retinol.

The formulation was applied to skin, and the pH of the skin was measured over time. Results are illustrated in FIG. 1.

EXAMPLE 2

A composition containing 0.15 percent by weight of retinol and 4 percent by weight of glycolic acid, neutralized with ammonium hydroxide to a pH of 6 was prepared.

An in vivo study of proliferative activity on skin was conducted. The marker of proliferative activity is an increase in fluorescent signal in the ultraviolet portion of the light spectrum. Over the course of 11 days of application, the fluorescence of the epidermis (exciting with 296 nm radiation, monitoring fluorescence at 340 nm) increases with increased proliferation activity. This fluorescence marker also increases after another proliferation inducing treatment such as tape-stripping, and has been shown to correlate with increased cell turnover-rate as measured by increased loss of epidermal stain, dansyl chloride.

Figure 2:
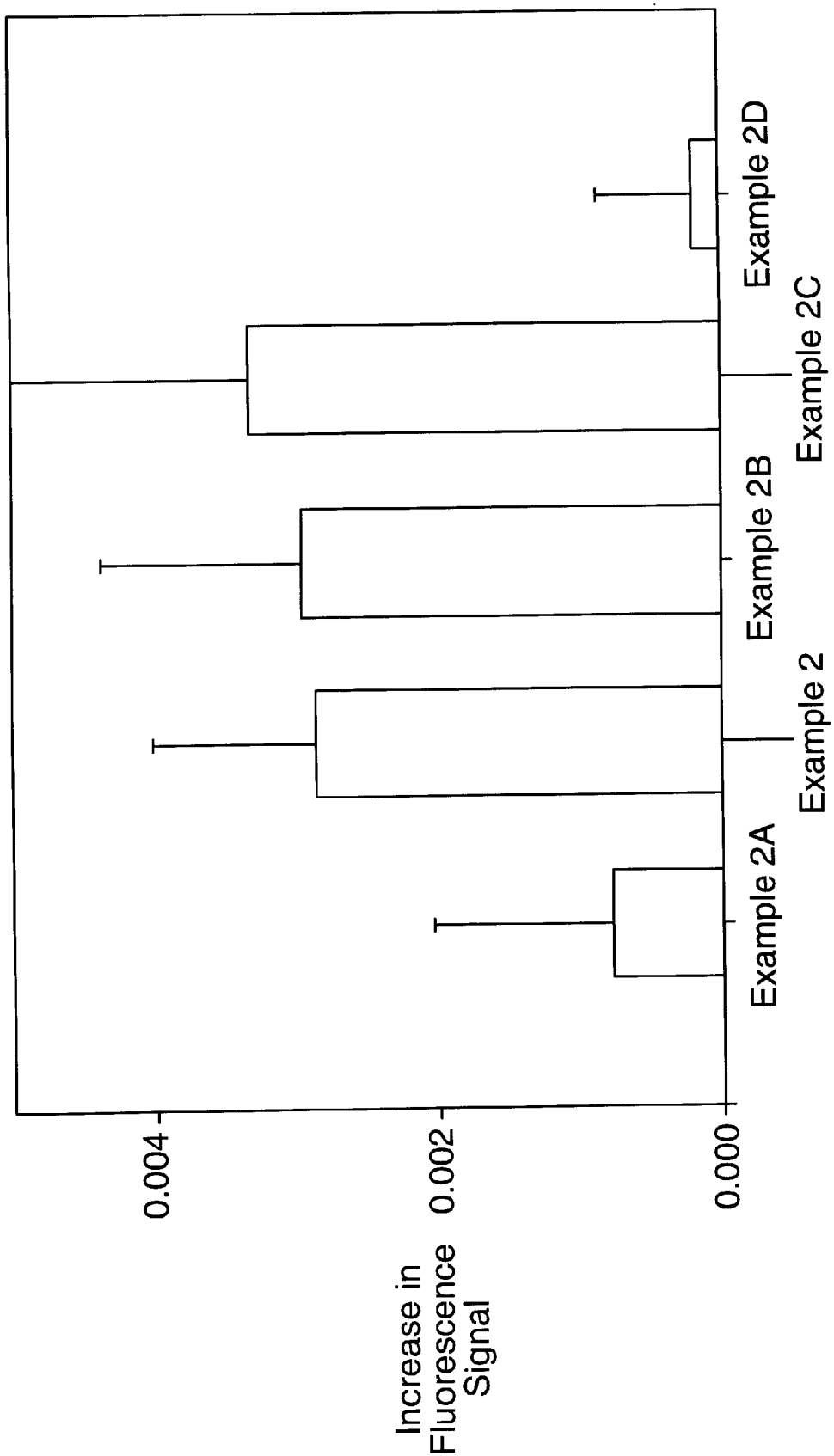
FIG. 2 is a graphic illustration of cell proliferation measured as slope of fluorescence after treatment.

The slope of the increased fluorescence is illustrated in FIG. 2.

COMPARATIVE EXAMPLE 2A

An in vivo study as described in Example 2 was conducted using a preparation containing no glycolic acid or retinol at pH 6 (placebo).

The slope of the increased fluorescence is illustrated in FIG. 2.

COMPARATIVE EXAMPLE 2B

An in vivo study as described in Example 2 was conducted using a preparation containing 4 percent by weight of partially neutralized glycolic acid at pH 4 without retinol (Avon ANEW®).

The slope of the increased fluorescence is illustrated in FIG. 2.

COMPARATIVE EXAMPLE 2C

An in vivo study as described in Example 2 was conducted using a preparation containing 8 percent by weight of glycolic acid partially neutralized at pH 3.8 without retinol (Neutrogena HEALTHY SKIN®).

The slope of the increased fluorescence is illustrated in FIG. 2.

COMPARATIVE EXAMPLE 2D

An in vivo study as described in Example 2 was conducted on untreated skin.

The slope of the increased fluorescence is illustrated in FIG. 2.

FIG. 2 illustrates a significant increase in fluorescence activity and, therefore, cell proliferation in the retinol/glycolic acid preparation of Example 2 in comparison with both a placebo and untreated skin.

FIG. 2 also illustrates a significant increase in fluorescence activity and, therefore, cell proliferation in the retinol/glycolic acid preparation of Example 2 which is similar to that of glycolic acid containing products having pH's of about 4 (Comparative Examples 2B–D).

EXAMPLE 3

A composition containing 0.15 percent by weight of retinol and 4 percent by weight of glycolic acid neutralized to pH 5.5 with ammonium hydroxide was prepared.

Figure 3:
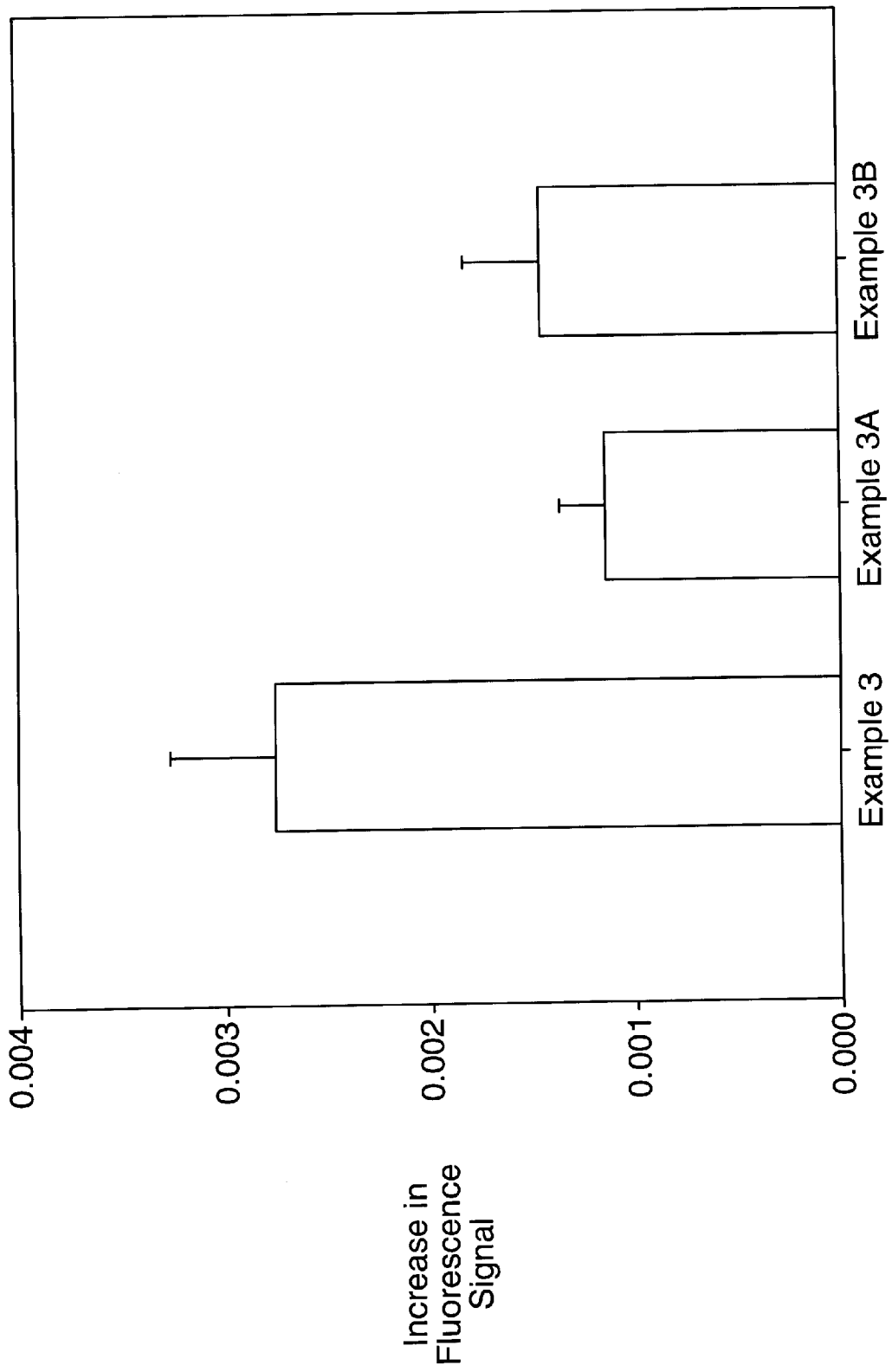
FIG. 3 is a graphic illustration comparing the activity of ammonium hydroxide and sodium hydroxide neutralized alpha-hydroxy acids in combination with retinol.

Fluorescence was measured as in Example 2. Results are illustrated in FIG. 3.

COMPARATIVE EXAMPLE 3A

A composition containing 0.5 percent by weight of retinol and 4 percent by weight of glycolic acid neutralized to pH 5.5 with sodium hydroxide was prepared.

Fluorescence was measured as in Example 2. Results are illustrated in FIG. 3.

COMPARATIVE EXAMPLE 3B

The fluorescence of untreated skin was measured as in Example 2. Results are illustrated in FIG. 3.

FIG. 3 illustrates that while ammonium glycolate (Example 3) dissociates when applied to the skin, sodium glycolate apparently does not (Comparative Example 3A). The latter results in little change in proliferative activity of the skin, and thus no apparent skin benefit.

EXAMPLE 4

A composition prepared as in Example 1 was stored for 13 weeks at 40° C. (simulating 2 years of ambient aging). This preparation retained 87% of the original retinol content after storage.

COMPARATIVE EXAMPLE 4A

A composition prepared in Comparative Example 1A was stored for 13 weeks at 40° C. (simulating 2 years of ambient aging). This preparation retained only 52% of the original retinol content after storage.

All patents, publications, applications, and test methods mentioned herein are hereby incorporated by reference.

Many variations of the present invention will suggest themselves to those skilled in the art in light of the above, detailed description. All such obvious variations are within the full intended scope of the appended claims.

What is claimed is:

1. A composition comprising:
   (A) a retinoid;
   (B) an acid selected from the group consisting of a hydroxy acid, ascorbic acid or a combination thereof;
   (C) an acid neutralizing effective amount of ammonium hydroxide, and
   (D) at least 0.1% by weight, of one or more antioxidants; wherein said composition has a pH from about 5 to about 6.

2. A composition as defined in claim 1, wherein said retinoid is selected from the group consisting of retinol, retinoic acid, and retinaldehyde.

3. A composition as defined in claim 2, wherein said retinoid is retinol.

4. A composition as defined in claim 1, wherein said retinoid is pH sensitive.

5. A composition as defined in claim 3, wherein said hydroxy acid is selected from the group consisting of alpha-hydroxy acid, a beta-hydroxy acid, a polyhydroxy acid, or any combination of any of the foregoing.

6. A composition as defined in claim 5, wherein said hydroxy acid is an alpha-hydroxy acid.

7. A composition as defined in claim 6, wherein said alpha-hydroxy acid is selected from the group consisting of glycolic acid, malic acid, tartaric acid, lactic acid, pyruvic acid, or any combination of any of the foregoing.

8. A composition as defined in claim 7, wherein said alpha-hydroxy acid is glycolic acid.

9. A composition as defined in claim 5, wherein said beta-hydroxy acid is salicylic acid.

10. A composition of claim 7, wherein said retinol comprises at least about 0.01 percent by weight, based upon 100 percent by weight of total composition.

11. A composition of claim 10, wherein the amount of said acid ranges from about 4 to about 12 percent by weight, based upon 100 percent by weight of total composition.

12. A composition as defined in claim 1, comprising a member of the group consisting of a multi-lamellar vesicle, a liposome, a nanosphere, a microsponge, or any combination of any of the foregoing.

13. A composition as defined in claim 1, further comprising:
   (D) a vehicle;
   (E) humectant;
   (F) a buffering agent;
   (G) a viscosity adjuster;
   (H) a preservative;
   (I) an emulsifier;
   (J) a conditioning agent;
   (K) an emollient;
   (L) a thickener;
   (M) an antioxidant;
   (N) a UV stabilizer;
   (O) a sunscreen filter;
   (P) a fragrance;
   (Q) a colorant; or
   (R) any combination of any of the foregoing.

14. A composition comprising:
   (A) a retinoid;
   (B) a neutralized ammonium salt of an acid selected from the group consisting of a hydroxy acid, ascorbic acid or a combination thereof, and
   (C) at least 0.1%, by weight, of one or more antioxidants; wherein said composition has a pH from about 5 to about 6.

15. A composition as defined in claim 14, wherein said retinoid is selected from the group consisting of retinol, retinoic acid, and retinaldehyde.

16. A composition as defined in claim 15, wherein said retinoid is retinol.

17. A composition as defined in claim 14, wherein said retinoid is pH sensitive.

18. A composition as defined in claim 16, wherein said acid is selected from the group consisting of an alpha-hydroxy acid, a beta-hydroxy acid, a polyhydroxy acid, or any combination of any of the foregoing.

19. A composition as defined in claim 18, wherein said hydroxy acid is an alpha-hydroxy acid.

20. A composition as defined in claim 19, wherein said alpha-hydroxy acid is selected from the group consisting of glycolic acid, malic acid, tartaric acid, lactic acid, pyruvic acid, or any combination of any of the foregoing.

21. A composition as defined in claim 20, wherein said alpha hydroxy acid is glycolic acid.

22. A composition as defined in claim 18, wherein said beta-hydroxy acid is salicylic acid.

23. A composition of claim 20, wherein said retinol comprises at least about 0.01 percent by weight, based upon 100 percent by weight of total composition.

24. A composition of claim 23, wherein the amount of said neutralized ammonium salt of an acid ranges from about 4 to about 12 percent by weight, based upon 100 percent by weight of total composition.

25. A composition as defined in claim 14 comprising a liposome.

26. A composition as defined in claim 18, further comprising:
   (C) vehicle;
   (D) a humectant;
   (E) a buffering agent;
   (F) a viscosity adjuster;
   (G) a preservative;
   (H) an emulsifier;
   (I) a conditioning agent;
   (J) an emollient;
   (K) a thickener;
   (L) an antioxidant;
   (M) a UV stabilizer;
   (N) a sunscreen filter;

(O) a fragrance;

(P) a colorant; or (Q) any combination of any of the foregoing.

27. A method for reducing fine lines and wrinkles and for increasing the clarity of a skin surface, cellular turnover, skin radiance, skin smoothness, skin permeation, or collagen synthesis in a mammal in need thereof, said method comprising topically administering a composition as defined in claim 1 to said animal.

28. A method for reducing fine lines and wrinkles and for increasing the clarity of a skin surface, cellular turnover, skin radiance, skin smoothness, skin permeation, or collagen synthesis in a mammal in need thereof, said method comprising topically administering a composition as defined in claim 18 to said animal.

29. A composition of claim 1, wherein at least one or said one or more antioxidants is BHT or tocopheryl acetate.

30. A composition of claim 8, wherein at least one or said one or more antioxidants is BHT or tocopheryl acetate.

31. A composition of claim 9, wherein at least one or said one or more antioxidants is BHT or tocopheryl acetate.

32. A composition of claim 14, wherein at least one or said one or more antioxidants is BHT or tocopheryl acetate.

33. A composition of claim 21, wherein at least one or said one or more antioxidants is BHT or tocopheryl acetate.

34. A composition of claim 22, wherein at least one or said one or more antioxidants is BHT or tocopheryl acetate.

35. A composition of claim 9, wherein said retinol comprises at least about 0.01 percent by weight, based upon 100 percent by weight of the total composition.

36. A composition of claim 35, wherein the amount of said acid ranges from about 4 to about 12 percent by weight, based upon 100 percent by weight of total composition.

37. A composition of claim 22, wherein said retinol comprises at least about 0.01 percent by weight, based upon 100 percent by weight of the total composition.

38. A composition of claim 37, wherein the amount of said neutralized ammonium salt of an acid ranges from about 4 to about 12 percent by weight, based upon 100 percent by weight of total composition.

* * * * *